United States Patent
Stanley et al.

(10) Patent No.: US 8,952,211 B2
(45) Date of Patent: Feb. 10, 2015

(54) ABSORBER DEMETHANIZER FOR FCC PROCESS

(71) Applicant: Lummus Technology Inc., Bloomfield, NJ (US)

(72) Inventors: Stephen J. Stanley, Matawan, NJ (US); Stephen De Haan, Wayne, NJ (US); Peter Daniel Kuzma, Jr., Bloomingdale, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 13/846,261

(22) Filed: Mar. 18, 2013

(65) Prior Publication Data

US 2013/0213794 A1    Aug. 22, 2013

Related U.S. Application Data

(63) Continuation of application No. 12/952,952, filed on Nov. 23, 2010, now Pat. No. 8,445,740, which is a continuation-in-part of application No. 12/260,751, filed on Oct. 29, 2008, now Pat. No. 8,399,728.

(51) Int. Cl.
*C10G 53/08* (2006.01)
*C07C 7/08* (2006.01)
(Continued)

(52) U.S. Cl.
CPC ............ *C07C 7/08* (2013.01); *C07C 7/1485* (2013.01); *C10G 9/00* (2013.01); *C10G 9/36* (2013.01); *C10G 11/18* (2013.01); *C10G 21/06* (2013.01); *C10G 25/05* (2013.01); *C10G 53/08* (2013.01);
(Continued)

(58) Field of Classification Search
CPC .......................... C07C 7/08; C07C 7/14883
See application file for complete search history.

(56) References Cited

U.S. PATENT DOCUMENTS

| 5,710,357 A | 1/1998 | Grenoble et al. |
| 5,811,621 A | 9/1998 | Van Dijk |

(Continued)

FOREIGN PATENT DOCUMENTS

| CA | 1165333 A1 | 4/1984 |
| EP | 0289233 A1 | 11/1988 |

(Continued)

OTHER PUBLICATIONS

Examination Report issued in corresponding Malaysian Application No. PI 2010005354 dated Feb. 28, 2013 (3 pages).

(Continued)

*Primary Examiner* — Tam M Nguyen
(74) *Attorney, Agent, or Firm* — Osha Liang LLP

(57) ABSTRACT

A process for recovering ethylene is disclosed, the process including: recovering a ethylene-containing stream comprising methane, ethylene, and nitrogen oxides from at least one of an ethylene production process and an ethylene recovery process; separating the ethylene-containing stream via extractive distillation using at least one $C_{2+}$ hydrocarbon absorbent to produce an overheads fraction comprising methane and nitrogen oxides and a bottoms fraction comprising the at least one $C_{2+}$ hydrocarbon absorbent and ethylene; wherein the separating comprises operating the extractive distillation at temperatures and pressures sufficient to prevent any substantial conversion of nitrogen oxides to $N_2O_3$.

21 Claims, 1 Drawing Sheet

(51) Int. Cl.
  *C07C 7/148* (2006.01)
  *C10G 9/00* (2006.01)
  *C10G 9/36* (2006.01)
  *C10G 11/18* (2006.01)
  *C10G 21/06* (2006.01)
  *C10G 25/05* (2006.01)

(52) U.S. Cl.
  CPC .... *C10G 2300/4081* (2013.01); *C10G 2400/20* (2013.01)
  USPC .............................. 585/867; 585/864; 585/833

(56) References Cited

U.S. PATENT DOCUMENTS

| | | |
|---|---|---|
| 7,707,852 B2 | 5/2010 | Wang et al. |
| 2004/0116757 A1 | 6/2004 | Van Egmond et al. |
| 2004/0211703 A1 | 10/2004 | Duhon et al. |
| 2008/0154007 A1 | 6/2008 | Mori et al. |

FOREIGN PATENT DOCUMENTS

| | | |
|---|---|---|
| JP | 080503197 A | 4/1996 |
| JP | 2008505987 A | 2/2008 |
| JP | 57197228 A | 12/2012 |
| WO | 2005017068 A2 | 2/2005 |
| WO | 2007036156 A1 | 4/2007 |
| WO | 2010053598 A1 | 5/2010 |

OTHER PUBLICATIONS

Office Action issued in corresponding Japanese Application No. 2011-534547 dated Apr. 23, 2013 (8 pages).
PCT Notification of Preliminary Report on Patentability and Written Opinion issued in corresponding International Application No. PCT/US2011/057278 dated Jun. 6, 2013 (7 pages).
Office Action issued in corresponding Japanese Application No. 2013-540950 with English translation dated Aug. 5, 2014 (7 pages).
Extended European Search Report issued in corresponding European Application No. 098251481 dated Jul. 23, 2014 (6 pages).
Examiner's Report issued in corresponding Chilean Application No. 1405-2009 with English language letter reporting the same dated May 28, 2013 (5 pages).

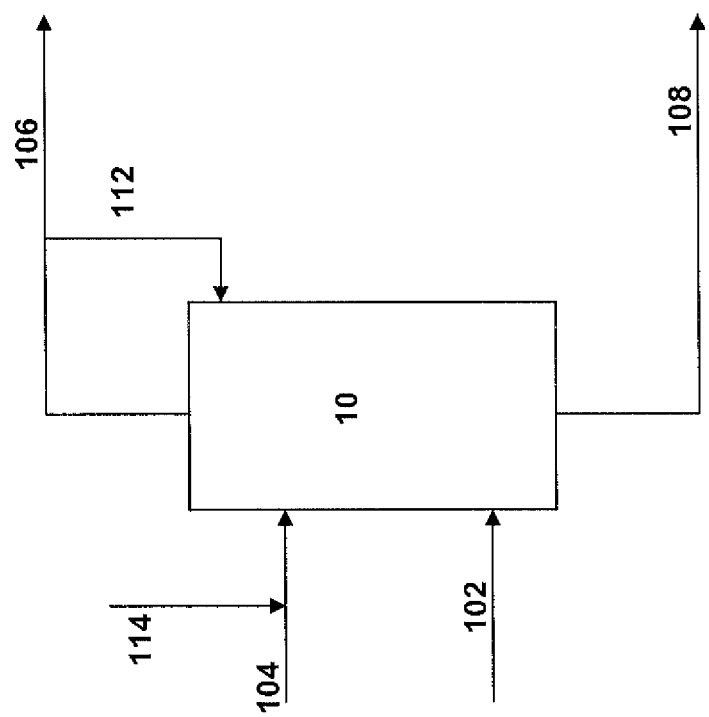

ABSORBER DEMETHANIZER FOR FCC PROCESS

CROSS-REFERENCE TO RELATED APPLICATION

This application is a continuation application and claims benefit under 35 U.S.C. §120 to U.S. patent application Ser. No. 12/952,952, filed Nov. 23, 2010 now U.S. Pat. No. 8,445,750, which is a continuation-in-part and claims priority pursuant to 35 U.S.C. §120, to U.S. patent application Ser. No. 12/260,751, filed Oct. 29, 2008, issued as U.S. Pat. No. 8,399,728, on Mar. 19, 2013. Those applications are incorporated herein by reference in their entirety.

FIELD OF THE DISCLOSURE

Embodiments disclosed herein relate generally to processes for recovering ethylene from streams resulting in various petrochemical processes. More specifically, embodiments disclosed herein relate to processes for recovering ethylene from ethylene-containing streams as may be result from ethylene-production or ethylene-recovery processes, where the ethylene-containing stream may contain one or more of carbon dioxide, water, and nitrogen oxides. Even more specifically, embodiments disclosed herein relate to the recovery of ethylene from streams containing methane and nitrogen oxides at conditions to avoid substantial formation of $N_2O_3$.

BACKGROUND

Ethylene is an extremely valuable commodity chemical for producing various chemical and polymer products used in numerous commercial as well as consumer products and applications. Ethylene may be produced in a number of petrochemical processes, including methanol-to-olefins (MTO) processes, fluid catalytic cracking processes (FCC), as well as thermal and steam cracking processes. These processes typically result in an effluent containing a mixture of hydrocarbons, as well as one or more of nitrogen, carbon dioxide, nitroxides, methane, ethane, and other hydrocarbons.

Before the ethylene produced can be sold and used, it is necessary to employ a process which recovers the ethylene component in a desirable, ethylene-rich stream by separating it from other components and impurities. Many times this separation is integrated with existing olefins plants but in certain instances, such as where off-gas flow rates are large enough, stand-alone units have also been operated. Because of the high quantity of lighter components such as hydrogen, nitrogen, and methane, the feed gases are typically compressed from pressure of about 1.17 to 1.38 MPa gauge (170 to 200 psig) to pressures around 3.45 MPa gauge (500 psig) in multi-stage feed gas compressors. The compression step allows for the recovery of 90% to 99% of the ethylene and heavier materials contained in the feed gases using a combination of mechanical refrigeration and expansion of the methane and lighter portions of the feed gas after demethanization. However, the capital and operating costs for the feed gas compressors are very high.

Further, the processing of refinery off-gases for olefin recovery has associated safety concerns because nitrogen oxide is also present in trace amounts in the refinery offgas streams. The nitrogen oxide easily oxidizes forming nitrogen dioxide. Nitrogen oxides, for example NO and $NO_2$, are commonly referred to as NOx. Mixtures of nitrogen oxide and nitrogen dioxide can form dinitrogen trioxide ($N_2O_3$) at temperatures below $-21°$ C. $N_2O_3$ and heavier diolefins ($C_4+$) can react at these low temperatures forming nitrated gums which are unstable and can explode if thermally or mechanically shocked.

A typical process for low pressure olefins recovery from fluid catalytic cracker (FCC) offgas is disclosed in U.S. Pat. No. 5,502,971, which is hereby incorporated in its entirety. U.S. Pat. No. 5,502,971 describes a low pressure cryogenic technique for recovering $C_2$ and heavier hydrocarbons from a refinery off-gas by eliminating feed gas compression and high pressures while maintaining recovery of $C_2$ and heavier hydrocarbons at temperatures above temperatures at which nitrated gums can form.

One process for the separating and recovering of ethylene from a process effluent involves the use of flash stages and distillation at cryogenic temperatures, as described in U.S. Pat. Nos. 7,166,757 and 4,499,327. As described therein, the current state of the art ethylene recovery and separation processes which dominate the industry involve cryogenic boiling point separation of ethylene and methane at temperatures that may be lower than $-90°$ C. The cryogenic separation can be very expensive due to both the capital cost of the specialized vessel metallurgy and refrigeration equipment, and the operating costs, including compression and cooling for the energy-intensive chill train.

As discussed, the use of cryogenic temperatures during the processes for treating refinery off-gas or process effluents can result in unstable and potentially dangerous operating conditions. For example, the NOx present in the refinery off-gas can react to form $N_2O_3$. Further, it has been found that the $N_2O_3$ formation rate significantly increases with decreasing temperature, thus making a cryogenic process especially susceptible. $N_2O_3$ is a highly oxidative compound, which can form highly unstable and highly reactive gums upon contact with poly-unsaturated compounds, such as butadiene. Even at cryogenic temperatures and at concentrations in the ppb levels, such unstable gums can accumulate and cause dangerous runaway reactions and even explosions.

Accordingly, there exists a need for an improved method of separating methane to recover ethylene and other valuable products from refinery offgas that reduces the capital and operating costs and improves the operation safety and stability.

SUMMARY OF THE DISCLOSURE

In one aspect, embodiments disclosed herein relate to a process for recovering ethylene, the process including: recovering a ethylene-containing stream comprising methane, ethylene, and nitrogen oxides from at least one of an ethylene production process and an ethylene recovery process; separating the ethylene-containing stream via extractive distillation using at least one $C_{2+}$ hydrocarbon absorbent to produce an overheads fraction comprising methane and nitrogen oxides and a bottoms fraction comprising the at least one $C_{2+}$ hydrocarbon absorbent and ethylene; wherein the separating comprises operating the extractive distillation at temperatures and pressures sufficient to prevent any substantial conversion of nitrogen oxides to $N_2O_3$.

Other aspects and advantages will be apparent from the following description and the appended claims.

BRIEF DESCRIPTION OF DRAWINGS

FIG. 1 is a simplified flow diagram of a process for recovering ethylene according to embodiments disclosed herein.

DETAILED DESCRIPTION

Embodiments disclosed herein relate generally to processes for recovering ethylene from streams resulting in various petrochemical processes. More specifically, embodiments disclosed herein relate to processes for recovering ethylene from ethylene-containing streams as may be result from ethylene-production or ethylene-recovery processes, where the ethylene-containing stream may contain one or more of carbon dioxide, water, and nitrogen oxides ($NO_x$). Even more specifically, embodiments disclosed herein relate to the recovery of ethylene from streams containing methane and nitrogen oxides at conditions to avoid substantial conversion of nitrogen oxides to $N_2O_3$. As used in embodiments disclosed herein, the term "substantial conversion" in reference to nitrogen oxides refers to the formation and/or accumulation of $N_2O_3$ at levels greater than 10 ppb in some embodiments, greater than 5 ppb in other embodiments, and greater than 1 ppb in yet other embodiments. Conversely, "prevention of any substantial conversion" or like terminology refers to the prevention of the formation and/or accumulation of $N_2O_3$ at levels greater than 10 ppb in some embodiments, greater than 5 ppb in other embodiments, and greater than 1 ppb in yet other embodiments.

Ethylene-containing streams containing methane, nitrogen oxides, and ethylene useful in embodiments disclosed herein may be produced in any number of petrochemical processes, and may include effluents or off-gases from a fluid catalytic cracking system, a thermal cracking system; a thermal or steam cracking system, a methanol-to-olefins process, coker processes, visbreaker processes, or combinations thereof. For example, dilute ethylene from a FCC unit may contain very large quantities of hydrogen or methane, if they are not separated at a FCC vapor recovery unit by compression and distillation of FCC off-gas.

The various ethylene production and recovery processes noted above may produce streams including one or more $C_2^+$ streams. In one embodiment, the stream is comprised of $C_2$ to $C_{30}$ olefins and/or diolefins. In some embodiments, olefins in these ethylene-containing streams may include one or more of $C_2$ to $C_8$ olefins. In other embodiments, olefins in these ethylene-containing streams may include one or more of $C_2$ to $C_6$ olefins. In yet other embodiments, olefins in these ethylene-containing streams may include one or more of $C_2$ to $C_4$ olefins, for example, ethylene and propylene. In still other embodiments, olefins in these ethylene-containing streams may consist essentially of ethylene.

In some embodiments, the concentration of ethylene in the ethylene-containing streams may be at least approximately 5 mole percent. In other embodiments, the concentration of ethylene in the ethylene-containing streams may be at least approximately 10 mole percent. In yet other embodiments, the concentration of ethylene in the ethylene-containing streams may be at least approximately 20 mole percent. In still other embodiments, the concentration of ethylene in the ethylene-containing streams may be at least approximately 30 mole percent.

In some embodiments, the concentration of methane in the ethylene-containing streams may be less than approximately 90 mole percent. In other embodiments, the concentration of methane in the ethylene-containing streams may be less than approximately 80 mole percent. In yet other embodiments, the concentration of methane in the ethylene-containing streams may be less than approximately 70 mole percent. In still other embodiments, the concentration of methane in the ethylene-containing streams may be less than approximately 50, 40, 30, 20, or 10 mole percent. In other embodiments, the concentration of methane in the ethylene-containing stream may be less than approximately 2 mole percent.

In order to recover ethylene of sufficient purity, the reactor effluents and off-gases may undergo one or more separation stages. For example, it may be desired or necessary to separate ethylene from various reactants and products, including but not limited to, ethers and alcohols, carbon dioxide, water, methane, nitrogen oxides, and other reactants, reaction products and by-products, and diluents.

Most hydrocarbon products, byproducts, diluents, and impurities may be separated from the ethylene in the reactor effluents and off-gases via fractional distillation at non-cryogenic temperatures. For example, a de-propanizer may be used to separate $C_3$ and heavier materials, and a de-ethanizer may be used to separate ethane and heavier materials from ethylene and lighter materials. In some embodiments, the temperatures for such non-cryogenic separations may be higher than approximately $-90°$ C. In other embodiments, the temperatures may be higher than approximately $-60°$ C. In yet other embodiments, the temperatures may be higher than approximately $-40°$ C.

A particularly challenging separation is that of ethylene from methane and other lights (hydrogen, nitrogen, etc.) that may be contained within the reactor effluents and off-gases due to their low boiling points. Separating these components using fractional distillation would potentially require cryogenic temperatures less than $-90°$ C. or $-100°$ C. For example, such temperatures may be achieved via a closed-loop refrigeration system using a specialized refrigerant fluid, an additional refrigeration compressor, and a refrigeration loop.

However, olefin-containing streams produced via such refinery processes may inevitably contain trace amounts of nitrogen oxides, including NO and $NO_2$. Typically, nitrogen oxides are inert; however, under appropriate conditions, such as temperatures below about $-21°$ C., these compounds may further react to form $N_2O_3$, which is highly reactive. For example, even trace amounts of $N_2O_3$ may combine and react with poly-unsaturated olefins, such as butadiene present in an olefin-containing stream, to form highly unstable gum compounds. At temperatures greater than about $-50°$ C., the rate of $N_2O_3$ formation may be negligible. However, it has been found by the present inventors that the conversion of nitrogen oxides, including NO and $NO_2$, to $N_2O_3$ increases with a decrease in temperature, and may become substantial at cryogenic temperatures, for example, at temperatures of less than $-90°$ C. Therefore, traditional methods for separating ethylene from nitroxide-containing streams using cryogenic flash stages and distillation may pose safety and operability concerns. Nitroxides and the potential formation of $N_2O_3$ are a major safety and operability concern in cryogenic recovery systems, which often operate at temperatures below about $-100°$ C., as they may cause runaway reactions and even explosions.

It has been found that a hydrocarbon absorbent, such as a $C_{2+}$ hydrocarbon absorbent, can be effectively used as an absorbent to separate and recover the ethylene from the ethylene-containing streams at non-cryogenic temperatures. For example, ethylene-containing streams according to embodiments disclosed herein can be contacted with a hydrocarbon absorbent in an extractive distillation system, whereby at least a portion of the ethylene is absorbed by the hydrocarbon absorbent. The methane and lighter materials may be recovered as an overheads fraction, and the ethylene and the $C_{2+}$ hydrocarbon absorbent may be recovered as a bottoms fraction. In some embodiments, the hydrocarbon absorbent may be a $C_{2+}$ hydrocarbon, for example, including at least one of ethane, propane, propylene, one or more butanes (n-butane, isobutane, etc), one or more butenes, one or more pentenes, and one or more pentanes. In other embodiments, the hydrocarbon absorbent may consist essentially of propane.

Using a $C_{2+}$ hydrocarbon absorbent to separate ethylene from nitrogen oxides-containing streams at temperatures sufficient to prevent or reduce formation and accumulation of $N_2O_3$ according to embodiments disclosed herein provides a viable alternative to the traditional cryogenic separation process. In particular, a $C_{2+}$ hydrocarbon absorbent may be used to separate an ethylene-containing stream produced, for example, via a FCC process, a coker process, a methanol-to-olefins process, or other processes that may produce an effluent or off-gas containing NOx, methane and other light gases.

In some embodiments, ethylene recovery systems useful in embodiments disclosed herein may include one or more absorber stages. For example, the ethylene-containing stream may be contacted with the hydrocarbon absorbent in one or more absorber stages arranged in series within a single column or in a series of multiple columns.

In some embodiments, the ethylene recovery systems may include one or more extractive distillation and/or distillation stages. For example, the ethylene-containing streams may be contacted with the hydrocarbon absorbent in one or more extractive distillation and/or distillation stages arranged in series within a single column or in a series of multiple columns.

The one or more extractive distillation and/or distillation stages may comprise trays and/or packing for providing a sufficient surface area for the contacting. In some embodiments, the ethylene-containing streams and the hydrocarbon absorbent may be contacted counter-currently in the separation system. In other embodiments, the ethylene-containing streams and the hydrocarbon absorbent may be contacted co-currently in the separation system.

In some embodiments, at least 70 percent of the ethylene in the reactor effluent or off-gas may be absorbed and recovered from the extractive distillation system as a bottoms fraction along with the hydrocarbon absorbent; at least 80 percent of the ethylene may be absorbed and recovered in other embodiments; and at least 90 percent of the ethylene may be absorbed and recovered in yet other embodiments.

The bottoms fraction may be further separated to recover an ethylene-rich fraction from the hydrocarbon absorbent, such as a $C_{2+}$ hydrocarbon absorbent. For example, the ethylene-rich fraction may be separated from the $C_{2+}$ hydrocarbon absorbent using fractional distillation. The concentration of ethylene in the ethylene-rich fraction may vary, depending upon the desired end use. In some embodiments, the bottoms fraction may be separated to form an ethylene fraction and a hydrocarbon fraction including at least one of $C_{2+}$ hydrocarbon heavier than ethylene. In other embodiments, the bottoms fraction may be separated to form light hydrocarbon fraction containing ethylene and ethane, and a hydrocarbon fraction containing at least one $C_{3+}$ hydrocarbon.

As used herein, "rich" fractions contain at least 50% by weight of the indicated component. In some embodiments, the ethylene-rich fraction may contain at least 90% ethylene; at least 95% ethylene in other embodiments; at least 98% ethylene in other embodiments; at least 99% ethylene in other embodiments; at least 99.5% ethylene in other embodiments; and at least 99.8% ethylene in yet other embodiments. The targeted concentration of the indicated component in the streams may depend upon downstream requirements; for example, where the ethylene is to be used in a polymerization process, "polymer grade" ethylene, containing greater than 99% by weight ethylene, may be required.

In some embodiments, the concentration of the carried over hydrocarbon absorbent recovered in the overheads fraction along with methane from the extractive distillation system is less than approximately 30 mole percent. In other embodiments, the concentration of the carried over hydrocarbon absorbent recovered in the overheads fraction along with methane from the extractive distillation system is less than approximately 15 mole percent. In yet other embodiments, the concentration of the carried over hydrocarbon absorbent recovered in the overheads fraction along with methane from the extractive distillation system is less than approximately 10 mole percent. In still other embodiments, the concentration of the carried over hydrocarbon absorbent recovered in the overheads fraction along with methane from the extractive distillation system is less than approximately 5 mole percent.

Embodiments disclosed herein maintain pressure and temperature inside the absorber or extractive distillation system sufficient to prevent any significant formation of $N_2O_3$ from nitrogen oxides, including NO and $NO_2$, present in the ethylene-containing streams. As discussed above, it has been found that the rate of $N_2O_3$ formation becomes significant at temperatures below approximately $-90°$ C. Thus, by avoiding cryogenic process temperatures of approximately $-90°$ C. and below, for example, by using a hydrocarbon absorption process according to embodiments disclosed herein, the formation of $N_2O_3$ may be prevented or significantly reduced.

In some embodiments, the absorber or extractive distillation system may be operated at an overheads temperature of $-90°$ C. or greater; at an overheads temperature of $-50°$ C. or greater in other embodiments; $-40°$ C. or greater in other embodiments; $-20°$ C. or greater in other embodiments; $-10°$ C. or greater in other embodiments; and at an overheads temperature of $0°$ C. or greater in yet other embodiments.

In general, the overheads pressure inside the absorber or extractive distillation system may be maintained at a level required for the distillation and as required for absorption of ethylene into the hydrocarbon absorbent. In some embodiments, the overheads pressure inside the absorber or extractive distillation system may be in the range from 0.01 MPag to 10 MPag; in the range from 0.1 MPag to 4 MPag in other embodiments; from 0.5 MPag to 3 MPag in other embodiments; and the overheads pressure inside the absorber or extractive distillation system may be in the range from approximately 0.5 MPag to 1 MPag in yet other embodiments.

Referring now to FIG. 1, an extractive distillation process in accordance with embodiments disclosed herein is illustrated. For simplicity purposes, auxiliary equipment has been omitted from the figure. One of ordinary skill in the art would recognize that other equipment and devices, including but not limited to, pumps, compressors, heat exchangers, drums, vessels, reactors, flow lines, valves, and control loops, can also be used. For example, other features not illustrated in FIG. 1, including but not limited to, internal or external heat exchange loops on the extractive distillation column and other features that may be used and could appear in a Process & Instrumentation Diagram (P&ID) for embodiments disclosed herein, although not illustrated, may be used in accordance with embodiments disclosed herein.

An ethylene-containing stream may be supplied to an extractive distillation system 10 via flow line 102. The extractive distillation system 10 may be an absorption column in some embodiments of the invention and the ethylene-containing stream 102 may enter the extractive distillation system 10 at a suitable point in the system to effect the desired contact with the $C_{2+}$ hydrocarbon solvent fed via flow line 104. For example, the solvent stream 104 may be fed to the extractive distillation system 10 at a point above the inlet for stream 102, such that the hydrocarbon solvent flow is countercurrent to the methane, i.e., the solvent flows down the extractive distillation system to contact the ethylene-containing stream 102 countercurrently. As the hydrocarbon absorbent traverses down the column, ethylene is absorbed by the hydrocarbon absorbent. The hydrocarbon absorbent and the absorbed ethylene may be recovered from the column 10 as a bottoms fraction via flow line 108. The methane may be recovered from the column 10 as an overheads fraction via flow line 106. In some embodiments, at least a portion of the overheads fraction 106 may be returned to the column 10 as reflux via flow line 112.

The bottoms fraction 108 may be further treated (not shown in FIG. 1) to separate an ethylene-rich fraction containing ethylene and a hydrocarbon fraction containing the hydrocarbon absorbent. At least a portion of the hydrocarbon fraction may be recycled to the column 10 as the hydrocarbon absorbent 104 or a hydrocarbon absorbent make-up stream 114.

In some embodiments where the hydrocarbon absorbent is propane and the overheads fraction 106 from the column 10 comprises propane, at least a portion of the overheads fraction 106 may be used as fuel. For example, both the methane and the propane in the overheads fraction 106 may be sent to a fuel header. In other embodiments, at least a portion of the propane in the overheads fraction 106 may be compressed and recovered. In yet other embodiments, the overhead fraction 106 may be further treated in a vent condenser (not illustrated) to increase olefin (ethylene) recovery.

In addition to methane and nitroxides, as mentioned above, the ethylene-containing streams may contain one or more additional components, such as diluents and reaction byproducts, including helium, argon, nitrogen, carbon monoxide, carbon dioxide, water, paraffins such as methane, ethane, and propane, aromatic compounds, and mixtures thereof. Additionally, air may be entrained into an ethylene production or recovery process, for example, due to operation under partial vacuum conditions or as an impurity in one of the feedstock components. Ethylene-containing streams may also include non-olefin products, including but not limited to, paraffins, acetylenes, ethers, alcohols, and esters.

In some embodiments, at least a portion of the ethylene-containing streams may be fed to an extraction system for removing any oxygenates, such as methanol and/or ethers contained therein, using an aqueous solvent, such as water or glycol. An aqueous fraction having an increased concentration of methanol and ethers may be recovered from the extraction system. A hydrocarbon phase comprising methane and ethylene, and lean in methanol and ethers, may be recovered from the reactor effluent in the extraction system. The hydrocarbon phase may then be sent for further component separation(s). In some embodiments, the ethylene-containing streams may be compressed prior to any separation(s).

Carbon dioxide that may be present in the ethylene-containing streams may also require removal. For example, an olefin product specification may require removal of carbon dioxide from the ethylene-containing streams. Further, exposure of the carbon dioxide containing stream to below-sublimation temperatures may result in equipment damage and frozen piping. Methods commonly known and used in the industry, such as caustic solution treatment or amine absorption, may be used to remove $CO_2$ from the ethylene-containing streams. In some embodiments, ethylene-containing streams may be contacted with a caustic solution to separate at least a portion of the carbon dioxide present in the ethylene-containing streams. If necessary, the ethylene-containing streams may be compressed prior to the carbon dioxide removal stage.

The presence of water in ethylene-containing streams may lead to a number of problems. For example, cooling and/or compressing the ethylene-containing streams may result in formation of water condensate that can damage equipment and freeze pipes. Therefore, dehydration of the ethylene-containing streams to remove water using one of a number of techniques commonly used in the industry may be required or may be optionally performed based on process schemes and temperatures employed. In some embodiments, a molecular sieve dryer may be used for separating at least a portion of the water, drying the ethylene-containing streams. In other embodiments, a chemical desiccant such as glycol may be used for drying the ethylene-containing streams. In yet other embodiments, a portion of the water in the ethylene-containing streams may be condensed and the remaining ethylene-containing streams may be dried. Other dehydration techniques commonly known and used in the industry may also be used. If necessary, the ethylene-containing streams may be compressed prior to the water removal stage.

Advantages of processes according to embodiments disclosed herein may include improved operational safety and stability due to minimization of $N_2O_3$ formation from nitrogen oxides. As discussed above, trace amounts of nitrogen oxides, including NO and $NO_2$, present in the ethylene-containing streams can react to form $N_2O_3$, a highly oxidative compound which can in turn react with heavy unsaturated compounds, such as butadiene, present in the ethylene-containing streams to form unstable and highly reactive gums. Such gums, even at cryogenic temperatures and at ppb concentrations, can accumulate and cause dangerous runaway reactions and even explosions. As the rate of $N_2O_3$ formation drastically increases with decreasing temperature, and thus the cryogenic processes at temperatures lower than approximately $-90°$ C. currently used for separation of methane from ethylene-containing streams are a major safety concern. In contrast, Applicants have found that using hydrocarbon absorption to separate methane from ethylene-containing streams at temperatures of $-90°$ C. or higher is sufficient to prevent formation of $N_2O_3$.

Another advantage of processes according to embodiments disclosed herein may include reduced capital equipment cost. For example, the traditional cryogenic process, commonly referred to as the "chill train," requires specialized metallurgies and complicated refrigeration systems, including vessels, compressors, heat exchangers, circulation piping, and refrigerant costs. In contrast, as the present process is not conducted at cryogenic temperatures, less expensive metallurgy can be used and a number of equipment items associated with the chill train may be eliminated.

Processes according to embodiments disclosed herein may also advantageously reduce operating costs. For example, the energy costs of the refrigeration compression associated with the traditional cryogenic separation system may be considerably higher than those associated with a non-cryogenic extractive distillation process.

Still another possible advantage of recovering ethylene and/or heavier olefins from ethylene-containing streams according to embodiments disclosed herein may be that any portion of the $C_{2+}$ hydrocarbon absorbent, such as propane, entrained with the distillate, does not require additional compression and recovery, and instead may be sent directly to the process plant fuel header or otherwise may be used as a fuel. For example, in other demethanizer processes, the value of any residual $C_{2+}$ hydrocarbons may be too high to be sent to fuel; requiring additional compression and recovery facilities to recover the valued products. In contrast, the $C_{2+}$ hydrocarbons have no further use in the present processes, and thus may economically be sent to fuel.

Recovery of ethylene and/or heavier olefins from ethylene-containing streams according to embodiments may also reduced capital and operating costs due to reduced separation requirements for other non-olefin components present in an ethylene-containing streams. For example, limiting the process design to operating temperatures of $-90°$ C. and higher, and in some embodiments to temperatures of $-40°$ C. and higher, may eliminate the need for expensive methane refrigeration loops commonly used in cryogenic separation schemes. In contrast, using propane and/or propylene refrigeration to provide chilling for processes according to embodiments disclosed herein may substantially reduce capital investment costs, reduce operating costs, and improve reliability.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for recovering ethylene, the process comprising:
    recovering an ethylene-containing stream comprising methane, ethylene, and nitrogen oxides from at least one of an ethylene production process and an ethylene recovery process;
    separating the ethylene-containing stream via extractive distillation using an absorption solvent consisting essentially of $C_2$-$C_3$ hydrocarbon absorbent to produce an overheads fraction comprising methane and nitrogen oxides and a bottoms fraction comprising the solvent and ethylene;
    wherein the separating comprises operating the extractive distillation at non-cryogenic temperatures and at pressures sufficient for absorption of at least a portion of ethylene into the solvent; and
    wherein the process prevents any substantial conversion of the nitrogen oxides to $N_2O_3$.

2. The process of claim 1, wherein the ethylene-containing stream comprises at least one of an effluent from a fluid catalytic cracking system, an effluent from a thermal cracking system; an effluent from a steam cracking system, an off-gas from a fluid catalytic cracking system, an off-gas from a thermal cracking system, an off-gas from a steam cracking system, an off-gas from a methanol to olefins conversion system, or combinations thereof.

3. The process of claim 1, wherein the $C_2$-$C_3$ hydrocarbon absorbent comprises at least one of ethane, propane, propylene, and mixtures thereof.

4. The process of claim 1, further comprising operating the extractive distillation at an overheads temperature of $-90°$ C. or greater.

5. The process of claim 1, further comprising operating the extractive distillation at an overheads temperature of $-40°$ C. or greater.

6. The process of claim 1, further comprising operating the extractive distillation at an overheads pressure in the range from about 0.1 to about 4 MPag.

7. The process of claim 1, further comprising separating the bottoms fraction to form an ethylene fraction and a hydrocarbon fraction comprising the $C_2$-$C_3$ hydrocarbon absorbent.

8. The process of claim 7, further comprising recycling at least a portion of the hydrocarbon fraction to the extractive distillation.

9. The process of claim 1, further comprising separating the bottoms fraction to form a light hydrocarbon fraction comprising ethylene and ethane, and a hydrocarbon fraction comprising at least one $C_{3+}$ hydrocarbon.

10. The process of claim 2, further comprising at least one of:
    contacting the ethylene-containing stream with a caustic solution to separate at least a portion of any carbon dioxide contained in the ethylene-containing stream prior to the separating;
    contacting the ethylene-containing stream with a molecular sieve dryer to separate at least a portion of any water contained in the ethylene-containing stream prior to the separating;
    recovering an ethylene-containing stream having a reduced concentration of at least one of carbon dioxide and water; and
    feeding the ethylene-containing stream having a reduced concentration of at least one of carbon dioxide and water as the ethylene-containing stream fed to the separating.

11. The process of claim 1, further comprising:
    condensing and recycling at least a portion of the overheads fraction to the extractive distillation as a reflux.

12. The process of claim 1, further comprising treating the overheads fraction in a vent condenser to increase ethylene recovery.

13. The process of claim 1, wherein separating the ethylene-containing stream via extractive distillation further comprises contacting the ethylene-containing stream with the absorption solvent in a plurality of stages arranged in series within a single column.

14. The process of claim 1, wherein separating the ethylene-containing stream via extractive distillation further comprises contacting the ethylene-containing stream with the absorption solvent in a plurality of stages in a series of multiple columns.

15. A process for recovering ethylene, the process comprising:
    recovering an ethylene-containing stream comprising methane, ethylene, and nitrogen oxides from at least one of an ethylene production process and an ethylene recovery process;
    separating the ethylene-containing stream via extractive distillation, comprising contacting the ethylene-containing stream with a C2-C3 hydrocarbon absorption solvent in a plurality of stages at non-cryogenic temperatures and at pressures sufficient for absorption of at least a portion of ethylene into the solvent, the separating producing an overheads fraction comprising methane and nitrogen oxides and a bottoms fraction comprising the solvent and ethylene; and
    separating the bottoms fraction to form an ethylene fraction and a hydrocarbon fraction comprising the C2-C3 hydrocarbon absorbent;
    wherein the process prevents any substantial conversion of the nitrogen oxides to $N_2O_3$.

16. The process of claim 15, wherein the plurality of stages are either arranged in series within a single column or arranged in a series of multiple columns.

17. The process of claim 16, further comprising recycling at least a portion of the hydrocarbon fraction to the extractive distillation.

18. The process of claim 16, further comprising condensing and recycling at least a portion of the overheads fraction to the extractive distillation as a reflux.

19. A process for recovering ethylene, the process comprising:
   recovering an ethylene-containing stream comprising methane, ethylene, and nitrogen oxides from at least one of an ethylene production process and an ethylene recovery process;
   separating the ethylene-containing stream via extractive distillation using an absorption solvent consisting essentially of C2 hydrocarbon to produce an overheads fraction comprising methane and nitrogen oxides and a bottoms fraction comprising the solvent and ethylene;
   wherein the separating comprises operating the extractive distillation at non-cryogenic temperatures and at pressures sufficient for absorption of at least a portion of ethylene into the solvent; and
   wherein the process prevents any substantial conversion of the nitrogen oxides to $N_2O_3$.

20. The process of claim 19, wherein separating the ethylene-containing stream via extractive distillation further comprises contacting the ethylene-containing stream with the absorption solvent in a plurality of stages, said plurality of stages being either arranged in series within a single column or arranged in a series of multiple columns.

21. The process of claim 19, further comprising separating the bottoms fraction to form an ethylene fraction and a hydrocarbon fraction comprising the $C_2$ hydrocarbon absorbent.

\* \* \* \* \*